United States Patent [19]

Meyer et al.

[11] Patent Number: 4,973,489
[45] Date of Patent: Nov. 27, 1990

[54] POLYSACCHARIDE FATTY ACID POLYESTER FAT SUBSTITUTES

[75] Inventors: Richard S. Meyer, Tacoma; Casimir C. Akoh, Pullman, both of Wash.; Barry G. Swanson, Moscow, Id.; Daryl B. Winter, Seattle, Wash.; Jeffrey M. Root, Tacoma, Wash.; Michael L. Campbell, Kent, Wash.

[73] Assignee: Curtice Burns, Inc., Rochester, N.Y.

[21] Appl. No.: 153,632

[22] Filed: Feb. 8, 1988

Related U.S. Application Data

[63] Continuation-in-part of Ser. No. 49,625, May 13, 1987, abandoned.

[51] Int. Cl.$^5$ .............................................. A23D 9/00
[52] U.S. Cl. .................................... 426/611; 426/601; 426/607; 426/804; 536/4.1; 536/115
[58] Field of Search .............. 426/601, 607, 804, 611; 536/4.1, 115

[56] References Cited

U.S. PATENT DOCUMENTS

| | | |
|---|---|---|
| 2,831,856 | 4/1958 | Tucker et al. . |
| 3,558,597 | 1/1971 | von Brachel et al. . |
| 3,600,186 | 8/1971 | Mattson et al. . |
| 3,634,397 | 1/1972 | Thompson et al. . |
| 3,963,699 | 6/1976 | Rizzi et al. .................... 426/611 |
| 4,005,195 | 1/1977 | Jandacek . |
| 4,334,061 | 6/1982 | Bossier, III .................... 536/119 |
| 4,368,213 | 1/1983 | Hollenbach et al. . |
| 4,382,924 | 5/1983 | Berling et al. . |
| 4,461,782 | 7/1984 | Robbins et al. . |
| 4,508,746 | 4/1985 | Hamm . |
| 4,517,360 | 5/1985 | Volpenhein .................... 536/119 |
| 4,518,772 | 5/1985 | Volpenhein .................... 536/119 |

FOREIGN PATENT DOCUMENTS

| | | |
|---|---|---|
| 0233856 | 2/1987 | European Pat. Off. . |
| 0236288 | 2/1987 | European Pat. Off. . |
| 0254376 | 2/1988 | European Pat. Off. . |
| 0256585 | 2/1988 | European Pat. Off. . |
| 156263 | 8/1982 | Fed. Rep. of Germany . |

OTHER PUBLICATIONS

Hamm, D. J., "Preparation and Evaluation of Trialkoxytricarballylate, Trialkoxycitrate, Trialkoxyglycerylether, Jojoba Oil and Sucrose Polyester as Low Calories Replacements of Edible Fats and Oils", *Journal of Food Science*, 49:419–428, (1984).

*Primary Examiner*—Donald E. Czaja
*Assistant Examiner*—Evan Federman
*Attorney, Agent, or Firm*—Christensen, O'Connor, Johnson & Kindness

[57] ABSTRACT

A fat substitute food composition containing a polysaccharide fatty acid polyester in place of from about 0.5% to about 95% of the total fat content of the food composition is disclosed. The polysaccharide is a polymer of at least three monosaccharides and has at least four fatty acid ester groups, each fatty acid portion having from 4 to 24 carbon atoms.

6 Claims, No Drawings

POLYSACCHARIDE FATTY ACID POLYESTER FAT SUBSTITUTES

CROSS-REFERENCE TO RELATED APPLICATION

This application is a Continuation-in-Part application based on a prior copending application, Ser. No. 049,625 filed May 13, 1987, abandoned.

BACKGROUND OF THE INVENTION

Fats contribute from 30% to 40% of the total calories consumed by most Americans. One of the most common nutritional problems in the United States today is obesity, which results from the consumption of more calories than are expended. Consumption of fat is related to many disease states, such as heart disease. Successful reduction of fat consumption has not been achieved because of the dietary habits of the traditional American. Therefore, the search for fat substitutes or low-calorie fats has attracted attention in recent years.

Among the possible low-calorie fats or fat substitutes synthesized to date are sugar polyesters, polyglycerol esters, sucrose polyesters (SPE), neopentyl-type alcohols and other sugar derivatives such as sorbitol and mannitol, glycerol dialkyl ethers, triglyceride esters of alpha carboxylic acids, diglyceride esters of short-chain dibasic acids, trialkoxytricarballyate, polydextrose, palatinose, polygalactose, N-oil (tapioca dextrin), microbiologically derived products, nonabsorbable synthetic polymers with properties similar to edible oil, treederived products, low-metabolized natural fats and oils, biopolymers, branched polysaccharides and jojoba oil.

One method of reducing the caloric value of edible fats and retaining the characteristic functional physical properties of fats in foods is to prepare fatty acid esters of sugar or fatty acid esters of sugar alcohols that have reduced absorption and digestion. Absorption and digestion can be reduced by altering either the alcohol or fatty acid portion of the compound. In conventional synthesis procedures, for example, interesterification can be used to prepare sucrose polyesters. However, interesterification frequently requires high temperatures and toxic solvents such as dimethylacetamide, dimethylformamide, or dimethylsulfoxide. Therefore, conventional interesterification is not suitable for food applications.

Solvent-free, two-stage reaction sequences for making sucrose polyesters and avoiding the use of toxic solvents have been suggested. In the first stage, a 3:1 mole ratio of fatty acid methyl ester and sucrose is reacted in the presence of potassium soaps for forming a one-phase melt containing mainly esters of sucrose with a low degree of esterification. In the second stage, more methyl esters are added and reacted to produce a sucrose polyester in yields up to about 90% based on sucrose. This reaction is carried on the temperatures ranging from 130° C. to 150° C. It has been suggested that the sucrate ion generated with alkyl metal hydrides or sodium-potassium alloy catalyzes the sucrose polyester reactions. Modifications of this method have included adding methyl oleate at the beginning of the reaction and adding sucrose and sodium hydrides in increments. These modifications result in slightly different fatty acid composition and slightly lower degrees of esterification. About 80% to 90% yields of sucrose polyester have been achieved by reacting sucrose octaacetate and methyl palmitate in the presence of sodium or potassium at lower reaction temperatures, on the order of 110° C. to 120° C. In order to obtain 80% to 90% yields, however, the reaction must be continued for three to six hours.

SUMMARY OF THE INVENTION

The present invention provides a significantly improved process for the manufacture of saccharide fatty acid polyesters based on monosaccharides, disaccharides, sugar alcohols, trisaccharides, other polysaccharides, and glycosides. Emphasis is placed on the production of novel polysaccharide compounds, particularly trisaccharides that are found to be particularly efficacious as conventional fat substitutes. These saccharide fatty acid polyesters are also useful as emulsifiers or as fat substitutes in food compositions. The process comprises a one-stage, low-temperature, low-pressure process that produces relatively large yields of saccharide fatty acid polyesters. Basically, the process comprises the admixture of a lower acyl ester saccharide, a fatty acid lower alkyl ester, and an alkali metal catalyst to form a reaction mixture. The reaction mixture is then heated to a reaction temperature in the range of from 100° C. to 120° C. The reaction mixture is maintained at that temperature for a desired period of time, while a vacuum of less than 15 torr is drawn over the reaction mixture. By following this broadly outlined process, yields on the order of 95% to 99% of the saccharide fatty acid polyester can be achieved while only maintaining the reaction temperature for on the order of two hours. This process represents a significant improvement over prior art techniques of producing saccharide fatty acid polyesters.

DETAILED DESCRIPTION OF THE INVENTION

In its broadest sense, the process of the present invention for producing saccharide fatty acid polyesters is a solvent-free, single-step synthesis in which the reactants and catalysts are combined prior to heating. Additionally, a greater vacuum than has heretofore been used is drawn over the reaction mixture while it is being heated to the reaction temperature and during the time it is maintained at a reaction temperature. Finally, all reagents and implements of the reaction are scrupulously dried to prevent any saponification of any esters present in the reaction mixture.

The saccharide starting materials for the present invention include mono-, di-, tri-, tetra-, and higher polysaccharides. Also included in the definition of saccharides as utilized herein are the sugar alcohols. Examples of suitable sugar alcohols are mannitol, sorbitol, ribitols, and inositols. The most preferred sugar alcohol is sorbitol. Examples of suitable saccharides that can be utilized as starting materials are monosaccharides such as fructose, glucose, galactose, mannose, ribulose, rhamnose, xylulose, xylose, ribose, and arabinose. A preferred monosaccharide is glucose. Suitable disaccharides for use in conjunction with the method of the present invention include melibiose, lactose, maltose, sucrose, trehalose and cellobiose. The most preferred disaccharides include trehalose and sucrose. Trisaccharides utilized in accordance with the method of the present invention include raffinose, gentianose, 4'-galactosyl lactose and trisaccharides of galactose, mannose, glucose, and fructose. The most preferred trisaccharide is raffinose. Other suitable higher polysaccharides include stachyose, verbascose, the maltodextrins, corn syrup solids, zylans, glycogen, cellulose, amylose, agarose, the galactans, and mannans. The most preferred higher polysaccharides are stachyose and verbascose.

In order to be usable in accordance with the method of the present invention, hydroxyl groups on the saccharides are esterified to form lower acyl ester saccharides. By lower acyl is meant an acyl group having six or fewer carbon atoms. Preferably, acetyl and propionyl esters are employed. These lower acyl ester saccharides are formed so that all available hydroxyl groups are converted to esters by conventional methods. An example of a conventional method of esterification that can be employed is the method of Linstead, R. P., Rutenberg, A., Dauben, W.G., and Evans, W. L. *J. Am. Chem. Soc.*, 62:3260 (1940).

It has been found that nonreducing lower acyl ester saccharides are suitable reactants in accordance with the method of the present invention, without further modification. It is necessary, however, to convert any reducing saccharides into nonreducing saccharides, followed by formation of the corresponding lower acyl ester saccharides, in order to make them suitable for use in accordance with the method of the present invention. Conversion of reducing saccharides into nonreducing saccharides may be accomplished by either converting the reducing saccharide into a glycoside or by reducing the reducing saccharide to the corresponding alcohol. In the former case, the reducing saccharide is reacted with an alcohol to form the glycoside. Alcohols suitable for forming glycosides with reducing sugars include: alkyl, aryl, alkaryl, aralkyl, heteroalkyl, heteroaryl, polyacohols including sugars, and thiols. Preferred alcohols include one to six carbon alkyl alcohols. The most preferred alcohols are methanol and ethanol. Methyl glycosides of glucose can be made by reacting glucose with anhydrous methanol in the presence of HCl, by procedures well known in the art. Conversion of a reducing saccharide into the corresponding alcohol can be achieved by standart reducing techniques known to those skilled in the art. An exemplary technique is reduction with hydrogen gas and a metal catalyst such as nickel. Other equivalent reducing agents are also suitable. Preferred reducing saccharides suitable for reduction include the maltodextrins. Example of reduced saccharides that can be formed by reducing maltodextrins include maltitol, maltotriitol, and 4'-galactosyl lactitol. By 4'-galactosyl lactitol as used herein is meant the alcohol produced by the reduction of 4'-galactosyl lactose (see below). By maltotriitol as used herein is meant the alcohol produced by the reduction of the trisaccharide maltotriose.

Suitable acids for use in conjunction with the method of the present invention are the fatty acids having from 4 to 24 carbon atoms. Examples of fatty acids usable in accordance with the present invention are butyric, caprioc, caprylic, capric, lauric, myristic, myristoleic, palmitic, palmitoleic, stearic, oleic, ricinoleic, linoleic, linolenic, oleosteric, arachidic, behenic, erucic, arachidonic and lignoceric. Pure fatty acids or naturally occuring fats and oils can serve as a source of the fatty acid components for saccharide fatty acid esters produced in maintaining the reaction mixture of the reaction temperature for only about two to two and one-half hours. Not only is this yield better than prior art yields, but these yields are achieved in about half the time that the prior art took to achieve yields of less than 90%.

Novel compositions that have been produced in accordance with the present invention include the trisaccharide fatty acid polyester, raffinose fatty acid polyester; the disaccharide fatty acid polyester, trehalose fatty acid polyester; and the tetrasaccharide fatty acid polyester, stachyose fatty acid polyester. Novel compositions produced from reducing saccharides include maltitol fatty acid polyester and maltotriitol fatty acid polyester. These saccharide fatty acid polyesters, either alone or blended with other substances, are suitable fat or oil substitutes.

By saccharide fatty acid polyesters as used in this invention is meant saccharides in which four or more of the saccharide hydroxyl groups have been esterified with a fatty acid, and the resultant polyester has a melt point and consistency of an oil. Yields reported for saccharide fatty acid polyesters in this invention are based on $n-1$ or more saccharide hydroxyl groups being esterified with a fatty acid, where n is the maximum number of ester bonds possible for a given saccharide. For the novel trisaccharides prepared in this invention, ten or more saccharide hydroxyls must be esterified with fatty acids before they are counted as products in the percent yield calculation. Similarly, in the case of novel tetra saccharides, fifteen or more saccharide hydroxyls are fatty acid esterified and, for the novel disaccharide, seven or more saccharide hydroxyls are fatty acid esterified in the final calculated yield.

An example of a preferred homogeneous polyester of raffinose is raffinose undecapalmitate. Similarly, an example of a preferred homogeneous polyester of trehalose is trehalose octastearate. Heterogeneous saccharide polyesters may also be produced in accordance with the method of this invention by blending two or more fatty acid methyl esters in the reaction mixture in predetermined ratios. For example, raffinose undecaacetate, methyl palmitate and methyl stearate may be reacted in ratios of 1:5:6 by the process of this invention to produce a heteropolyester of raffinose containing both stearate and palmitate groups esterified to raffinose. Adjusting the ratios and composition of fatty acid methyl esters in the reaction mixture will produce blended saccharide fatty acid polyesters having particular properties.

Novel higher polysaccharide polyesters having one, two or three fatty acids esterified to the higher polysaccharide moiety are suitable for use as emulsifiers in food processing as well as in the cosmetic and pharmaceutical industry. By higher polysaccharide as used herein is meant tri-, tetra-, penta-, and larger oligosaccharides. Examples of higher polysaccharides suitable for esterification to produce novel emulsifiers include the trisaccharides, O-β-D-galactopyranosyl-(1→4)-O-β-D-galactopyranosyl-(1→4)-D-glucose, hereafter referred to as 4'-galactosyl lactose, gentianose, and melezitose; the tetrasaccharide stachyose; the pentasaccharides, verbascose and polydextrose; and oligosaccharides, maltodextrins with Dextrose Equivalent (D. E.) of 1, 5, 10, 15, and 20, and corn syrup solids with D. E. of 24, 35, and 42. Preferred higher polysaccharide precursors for synthesis of novel emulsifiers are 4'-galactosyl lactose, maltodextrin D. E. 10, and corn syrup solids D. E. 35. To produce the novel emulsifiers of the present invention, any of the above exemplary saccharides which are reducing saccharides must be first converted to nonreducing saccharides as described above. For example, 4'-galactosyl lactose must be converted to the corresponding glycoside or alcohol.

Fatty acid esters suitable for use in conjunction with synthesis of novel emulsifiers are those having from 4 to 24 carbon atoms, as previously described. It is preferred that fatty acids range from 14 to 18 carbon atoms in length.

The synthesis of novel higher polysaccharide polyesters having one to four fatty acids esterified to the higher polysaccharide moiety is carried out by the method of the present invention by lowering the ratio of fatty acid methyl ester to saccharide lower acyl ester in the transesterification process.

The molar ratio of fatty acid methyl ester to saccharide lower acyl ester ranges between 1:1 and 5:1. The preferred ratio is about 3 moles of fatty acid methyl ester per mole of saccharide lower acyl ester. Depending on the ratio of fatty acid methyl ester and the type of saccharide lower acyl ester employed, various proportions of mono-, di-, and triesters of saccharides are obtained.

The following examples are intended to be illustrative of the present invention and to teach one of ordinary skill how to make and use the invention. These examples are not intended in any way to limit the invention or otherwise limit the protection afforded by Letters Patent hereon.

EXAMPLE I

Methyl oleate (51 g, 0.1720 mole) was placed in a three-necked, round-bottomed flask equipped with a magnetic stirrer, stopcocks, a vacuum take-off line leading to a liquid nitrogen cold trap, manometer, two condensers, thermometers, a vacuum pump and purged with dry $N_2$ gas for 30 minutes. Raffinose undecaacetate (15 g, 0.0155 mole) was added and the $N_2$ purging continued for an additional 15 minutes. The mole ratio of methyl oleate to raffinose undecaacetate was 11:1. Sodium metal (2% of the reactants by weight, 1.3 g) was added. Heating was started with continuous stirring under dry nitrogen atmosphere. The reaction mixture was heated to 110° C. to 115° C. and pressure was maintained at 0 to 8 mm torr. Synthesis of polyesters required constant dispersion of liquid sodium, liquid carbohydrate or polyol acetate and liquid fatty acid methyl esters for optimal interesterification under $N_2$ gas. Interesterification was assumed to begin when catalytic sodium metal and raffinose undecaacetate melted and the reaction mixture became homogeneous. Interesterification was continued under constant conditions for two and one-half hours. Volatile methyl acetate was trapped in liquid nitrogen to drive the reaction toward raffinose esterification. Raffinose polyoleate was purified by a modification of the method of Hamm, *J. Food Sci.* 49:419 (1984). The crude raffinose polyoleate reaction mixture was neutralized with 1–3 mL of acetic acid, dissolved in hexane, stirred and bleached with activated charcoal. The reaction mixture was then filtered with Whatman No. 4 filter paper to remove charcoal particles, and the filtrate was washed with 6×400 mL aliquots of methanol, allowing enough time for separation. The more dense methanol insoluble layer containing raffinose polyoleate was separated, dried over anhydrous sodium sulfate and filtered with Whatman No. 4 filter paper. Methanol and hexane were evaporated from raffinose polyoleate by rotary evaporation to yield a neat oil. The yield of raffinose polyoleate was 98.7%. The color of the polyester was golden yellow, similar to corn oil.

EXAMPLE II

The procedure of Example I was repeated, substituting 63.26 g of soybean oil FAME for methyl oleate. The average molecular weight of soybean FAME was assumed to be about 278.01. Raffinose undecaacetate (20 g, 0.0207 mole) was added to the FAME. The yield of raffinose fatty acid polyester of soybean oil FAME was 99.3%. The color of the polyester was golden yellow.

EXAMPLE III

The procedure of Example I was repeated by combining methyl stearate (8.04 g), safflower oil FAME (32.16 g), raffinose undecaacetate (12.00 g) and 2% by weight Na (1.04 g). Interesterification was carried out as described at 105° C. to 110° C. for 2 hours. A raffinose polyester of 80:20 (w/w) blend of safflower oil FAME and methyl stearate was produced. Safflower oil used in this study contained about 80% C18:2. The aim of this example was to blend safflower oil (primarily unsaturated) and methyl stearate (saturated) fatty acids in the ratio of 4:1 (wt. %). The yield of the raffinose fatty acid polyester was 95.8%. The color of the polyester was pale yellow.

The foregoing procedure was repeated, except the reaction was scaled up by starting with higher amounts of raffinose undecaacetate, corn, cottonseed, safflower, peanut and sunflower oil methyl esters. The corresponding raffinose fatty acid polyesters were obtained in good yields.

EXAMPLE IV

Substantially anhydrous methyl stearate (4.34 g), safflower oil fatty acid methyl ester (FAME) (39.06 g), and sucrose octaacetate (12.5 g) were mixed with 2% by weight Na (1.12 g), based on the weight of the reactants. Interesterification was carried out under dry $N_2$ atmosphere by first gradually heating the reaction mixture to a temperature in the range of 105° C. to 110° C. and maintaining that temperature for two hours. The pressure over the reaction vessel was maintained at 0 to 5 torr. The mole ratio of the fatty acid methyl esters to sucrose octaacetate was 8:1. A sucrose fatty acid polyester of 90:10 (w/w) blend of safflower oil FAME and methyl stearate was produced. Crude sucrose fatty acid polyester was purified as described in Example I. The yield of sucrose polyester (SPE) was 99.6% based on the initial weight of sucrose octaacetate (SOAc). The color of the SPE was pale yellow, resembling the color of safflower and soybean oil.

The foregoing procedure was repeated, except the safflower oil FAME and methyl stearate blend was replaced by an equivalent amount of safflower oil FAME alone.

EXAMPLE V

Substantially anhydrous methyl oleate 97% pure (69.9 g, 0.2358 mole) and sucrose octaacetate (20 g, 0.0294 mole) and 2% Na (1.8 g) were mixed. Interesterification was carried out at 105° C. to 110° C. for two and one-half hours under the conditions set forth in Example I. The final mole ratio of methyl oleate to sucrose octaacetate was 8:1. The final yield of sucrose polyoleate was 99.8% and the color of SPE was golden yellow, similar to corn oil.

EXAMPLE VI

Substantially anhydrous soybean oil FAME (82 g, 0.2947 mole) and sucrose octaacetate (25 g, 0.0368 mole) were mixed with 2% by weight sodium metal (2.1 g). The mole ratio of soybean oil FAME to SOAc was 8:1. Interesterification was performed under dry $N_2$ atmosphere at 115° C. to 118° C. for three hours. The pressure was maintained at 0 to 5 torr. Purification of the crude SPE was performed essentially as described in Example I. The yield of pure SPE was 96.1%. The color of the purified SPE was pale yellow, similar to soybean and peanut oil.

EXAMPLE VII

Substantially anhydrous methyl oleate (52.43 g, 0.1768 mole) and trehalose octaacetate (TOAc) (15.00 g, 0.0221 mole) were mixed with 2% by weight sodium metal (1.36 g). The reactants were heated to form a homogeneous melt at 115° C. Interesterification was continued at constant conditions for one and one-half hours at 100° C. to 105° C. and 0 to 5 torr. The mole ratio of methyl oleate to trehalose octaacetate was 8:1. Purification of the crude trehalose polyoleate was conducted essentially as described in Example I. The yield of trehalose polyoleate was 97.5%, based on the initial weight of TOAc. The color of trehalose polyoleate was golden yellow, similar to corn oil, sucrose polyoleate and raffinose polyoleate.

The foregoing procedure was repeated; however, the methyl oleate was replaced by equivalent amounts of soybean, safflower, corn, sunflower and peanut oil methyl esters. The corresponding trehalose fatty acid polyesters were obtained.

EXAMPLE VIII

Substantially anhydrous methyl oleate (49.14 g, 0.0276 mole) and sorbitol hexaacetate (SOHAc) (15.00 g, 0.0345 mole) were mixed with 2% by weight sodium metal (1.22 g). The mole ratio of methyl oleate to SOHAc was 6:1. Interesterification was performed under dry $N_2$ atmosphere at 100° C. to 115° C. for two and one-half hours. The pressure over the reaction vessel was maintained at 0 to 5 torr. Purification of the crude sorbitol polyester was conducted essentially as described in Example I. The yield of sorbitol polyoleate was 95.8% based on the initial weight of SOHAc. The color of sorbitol polyoleate was pale yellow, similar to safflower and soybean oil.

The foregoing procedure was repeated, except the methyl oleate was replaced by equivalent amounts of soybean, safflower, corn and peanut oil methyl esters. The corresponding sorbitol fatty acid polyesters were obtained.

EXAMPLE IX

4'-galactosyl lactose is prepared by adding 1200 g lactose to a 10-liter jar fermentor containing 6 liters of a *Cryptococcus laurentii* broth containing neopeptone (10 g/L) and dextrose (20 g/L) at pH 5.6. The broth containing lactose is incubated at 25°–30° C. for 6 hours, after which it is centrifuged to remove the microorganisms. The eluate is chromatographed on an activated carbon column, concentrated, filtered and the 4'-galactosyl lactose is crystallized from ethanol.

EXAMPLE X

The methyl glycoside of 4'-galactosyl lactose is made by a procedure adapted from Haworth et al., *J. Chem. Soc.*, 113, 188 (1918). 30 g of 4'-galactosyl lactose produced as described in Example IX is dissolved in a minimum amount of hot water in a one liter reaction vessel. The vessel is flushed with nitrogen, and 14 ml of dimethyl sulfate is slowly added. 30 ml of 50% sodium hydroxide is added dropwise with a dropping funnel while mixture is vigorously stirred. After the sodium hydroxide is added, another 14 ml of dimethyl sulfate and 20 ml of sodium hydroxide is added over a 2 hour period. The mixture is mixed at room temperature overnight. The temperature of the mixture is raised to 100 C. for 30 minutes to decompose any unreacted dimethyl sulfate. The solution is cooled and neutralized to a pH of 7.0 with sulfuric acid. Enough methanol is added to precipitate sodium sulfate out of solution. The mixture is then filtered and the crude methyl glycoside is obtained by rotary evaporation. The crude methyl glycoside is purified by dissolving it in a minimum of water and recrystallizing with methanol several times. The methyl glycoside is frozen with liquid nitrogen and freeze dried. The methyl glycoside is then acetylated according to Linstead et al., *J. Am. Chem. Soc.* 62, 3260 (1940). Interesterification of the acetylated glycoside with methyl oleate is carried out by the method of Example I, yielding 4'-galactosyl lactose polyester methyl glycoside.

EXAMPLE XI

Stachyose tetradecaacetate (STAc) was prepared according to the method of Linstead et al., *J. Am. Chem. Soc.*, 62, 3260 (1940). Substantially anhydrous methyl oleate 97% pure (17.03 g, 0.0574 mole) and stachyose tetradecaacetate (STAc) (5 g, 0.0383 mole) and 2% Na (0.44 g) were admixed. Interesterification was carried out at 105° C.–110° C. for two and one-half hours under the conditions set forth in Example I. The final mole ratio of methyl oleate to stachyose tetradecaacetate was 15:1. The final yield of stachyose polyoleate was 99.8% and the color of stachyose polyoleate was golden yellow, similar to corn oil.

The foregoing procedure was repeated, except the reaction was scaled up by starting with higher amounts of stachyose tetradecaacetate, soybean, safflower, peanut, corn, sunflower and cottonseed oil methyl esters or blends of these with methyl stearate. The corresponding stachyose fatty acid polyesters were obtained in good yields even when the mole ratio of FAME to STAc was 13:1 or 14:1.

EXAMPLE XII

Deep Fat Frying

Low-calorie potato chips were produced by frying thin potato slices in raffinose fatty acid polyester cooking oil. For each potato chip, a 5-g aliquot of raffinose polyester prepared from safflower oil FAME as described in Example III was poured into a small glass cooking vessel and heated to approximately 360° F. Small potato slices, having a thickness of 2 to 3 mm and a diameter of 2 to 3 cm were added to the oil and fried until done. Low-calorie potato chips produced in this way had satisfactory texture and had a flavor similar to potato chips fried in peanut oil.

EXAMPLE XIII

The procedure described in Example XII is employed to produce low-calorie potato chips by substituting the same quality of trehalose fatty acid polyester for raffinose polyester as the frying oil.

EXAMPLE XIV

Spoonable White Salad Dressing

A low-calorie spoonable white salad dressing was prepared by replacing the oil in a typical recipe of this type with raffinose polyester prepared from safflower oil FAME. Mixing the ingredients in the proportions below produced a salad dressing with satisfactory consistency and taste.

| Ingredient | Percent by Weight |
| --- | --- |
| Raffinose fatty acid polyester | 30.0 |
| Starch paste | 60.0 |
| starch | |
| sugar | |
| salt | |
| vinegar | |
| water | |
| Egg yolk | 5.0 |
| Water | 3.9 |
| Vinegar | 1.0 |
| Gum | 0.1 |
| | 100.0 |

EXAMPLE XV

Italian Salad Dressing

A low-calorie Italian salad dressing was prepared by replacing the oil found in typical recipes of this type with raffinose fatty acid polyester prepared from safflower FAME as described in Example III.

| Ingredient | Percent by Weight |
| --- | --- |
| Raffinose fatty acid polyester | 40.00 |
| Water | 35.45 |
| Lemon juice | 5.80 |
| Vinegar (120 grain) | 13.00 |
| Salt | 3.50 |
| Starch | 0.80 |
| Garlic | 2.00 |
| Onion and garlic | 1.00 |
| Other spices | 0.25 |
| | 100.00 |

EXAMPLE XVI

Low-calorie salad dressing is produced by substituting the same percent by weight of trehalose polyester prepared as described in Example VII for the raffinose fatty acid polyester in the salad dressing recipe of Example XV.

EXAMPLE XVII

Raffinose Polyester Emulsifier

Raffinose polyester is prepared and purified as described in Example I with a mole ratio of methyl oleate to raffinose undecaacetate of 2:1 in the reaction mixture. Raffinose polyesters prepared in this way are used as emulsifiers.

EXAMPLE XVIII

Sour Cream

A nondairy sour cream is prepared by using raffinose fatty acid polyester as an emulsifier.

| Ingredients | Percent by Weight |
| --- | --- |
| Water | 60.47 |
| Partly hydrogenated soybean oil | 18.00 |
| Whey protein concentrate | 10.67 |
| Corn syrup solid 24 DE | 7.00 |
| Soy protein isolate | 2.00 |
| Raffinose polyester made according to Example XIX | 0.50 |
| Guar gum | 0.30 |
| Locust bean gum | 0.20 |
| Lactic acid | 0.80 |
| Natural flavoring | 0.03 |
| | 100.00 |

These ingredients are blended according to the following procedure: soybean oil and raffinose polyester, made according to Example XVII, are heated together until they melt. The dry ingredients are then blended in water until a homogeneous hydrated mixture is obtained. The oil and raffinose polyester melt is added to the hydrated mixture and blended at high speed. Lactic acid is then added, and the mixture is pasteurized at 160° F. for two minutes and homogenized in a two-stage pressurized homogenizer.

All of the saccharide fatty acid polyesters produced in accordance with the present invention are usable as substitutes for naturally occurring fats and oils. The process and the novel products produced have been described in conjuction with preferred embodiments. One of ordinary skill, after reviewing the foregoing specification, will be able to make various changes, substitutions of equivalents, and other alterations without departing from the broad concepts disclosed herein. It is therefore intended that protection afforded by Letters Patent hereon be limited only by the definition contained in the appended claims and equivalents thereof.

The embodiments of the invention in which an exclusive property or privilege is claimed are defined as follows:

1. A fat substitute food composition consisting essentially of nonfat ingredients and fat ingredients, wherein from about 0.5% to about 95% of the total fat content of the food composition comprises a polysaccharide fatty acid polyester, said polysaccharide being a polymer of at least three monosaccharides and having at least four fatty acid ester groups, each fatty acid having from 4 to 24 carbon atoms and said polysaccharide being derived from a reducing polysaccharide that has been converted into a non-reducing polysaccharide by formation of a $C_{1-6}$ alkyl glycoside or from a reducing polysaccharide that has been converted into its corresponding alcohol.

2. The composition of claim 1, wherein the polysaccharide fatty acid polyester is a fatty acid polyester of polysaccharides selected from the group consisting of: 4'-galactosyl lactose $C_{1-6}$ alkylglycoside, 4'-galactosyl lactitol, and maltotriitol.

3. The composition of claim 1, wherein the polysaccharide fatty acid polyester is a trisaccharide $C_{1-6}$ alkylglycoside fatty acid polyester.

4. The composition of claim 1, wherein the polysaccharide fatty acid polyester is completely esterified.

5. The composition of claim 1, wherein the fatty acid ester groups are a blend of fatty acid ester groups, the fatty acid portion of which has from 4 to 24 carbon atoms.

6. The composition of claim 3, wherein said polysaccharide fatty acid polyester is a trisaccharide $C_{1-6}$ alkyl glycoside, the monosaccharides forming said trisaccharide comprising a member of the group consisting of galactose, mannose, glucose and fructose.

* * * * *

UNITED STATES PATENT AND TRADEMARK OFFICE
CERTIFICATE OF CORRECTION

Page 1 of 2

PATENT NO. : 4,973,489
DATED : November 27, 1990
INVENTOR(S) : R.S. Meyer et al.

It is certified that error appears in the above-identified patent and that said Letters Patent is hereby corrected as shown below:

| Column | Line | |
|---|---|---|
| 1 | 24, 25 | "alcohols" should be --alcohols,-- |
| 1 | 32 | "treederived" should be --tree-derived-- |
| 3 | 46 | "Example" should be --Examples-- |
| 3 | 57, 58 | "caprioc" should be --caproic-- |
| 3 | 61, 62 | "occuring" should be --occurring-- |

3    64    after "in" insert --accordance with the present invention. Suitable fats and oils include coconut oil, palm kernel oil, babassu oils, corn oil, soybean oil, safflower seed oil, peanut oil, olive oil, palm oil, sunflower seed oil, sesame seed oil and cottonseed oil. Mixtures of fatty acids derived from soybean, safflower, corn, peanut and cottonseed oils are especially preferred, because they contain from about 14 to 18 carbon atoms. In general, it is preferred that the fatty acids range from 14 to 18 carbon atoms, because they are liquid at room temperature and because they do not volatilize at the interesterification temperatures and pressures. As with the saccharides, the fatty acids and oils are converted to lower alkyl fatty acid esters in accordance with conventional procedures before reacting with a lower acyl ester saccharide. It is preferred that the lower alkyl group contains less than six carbon atoms and, preferably, one or two carbon atoms, because they are good leaving groups.

Prior to combining the reactants, they are thoroughly dried by conventional procedures, for example, vacuum drying over anhydrous sodium or magnesium sulfate, followed by dry nitrogen purging. The substantially anhydrous fatty acid alkyl ester and lower acyl ester saccharides are combined in mole ratios of at least 4:1, and preferably from 6:1 to 15:1, depending on the saccharide. To achieve high yields in accordance with the present invention, a catalyst is combined with the reactants prior to heating. Suitable catalysts include the alkali metal catalysts. Sodium and potassium are the most preferred of the alkali metals. Catalysts can be used in amounts up to 5% by weight, but are preferably used in amounts on the order of 2% by weight.

(continued)

UNITED STATES PATENT AND TRADEMARK OFFICE
CERTIFICATE OF CORRECTION

PATENT NO. : 4,973,489
DATED : November 27, 1990
INVENTOR(S) : R.S. Meyer et al.

It is certified that error appears in the above-identified patent and that said Letters Patent is hereby corrected as shown below:

As mentioned above, in order to achieve the high yields possible in accordance with the present invention, all components of the reaction mixture must be combined at room or slightly elevated temperature. It is preferred that the reaction mixture be heated to a reaction temperature gradually, preferably a heating rate no greater than 3°C per minute. Preferably, reaction temperatures range from 100°C to 125°C, while the temperature range of 105°C to 115°C is most preferred. During the heating and maintenance of the reaction temperature, the area over the reaction vessel is evacuated and flooded with a dry, inert atmosphere. The inert atmosphere can comprise any inert gas, but nitrogen is preferred because of its cost and availability. In order to obtain the yields established in accordance with the present invention, the vacuum pulled over the reaction mixture must be less than 15 torr and, preferably, in the range of from 0 to 8 torr. Under these conditions, a 95% to 99% yield can be achieved while--

Signed and Sealed this

Twelfth Day of January, 1993

*Attest:*

DOUGLAS B. COMER

*Attesting Officer*      *Acting Commissioner of Patents and Trademarks*